Figure 1:
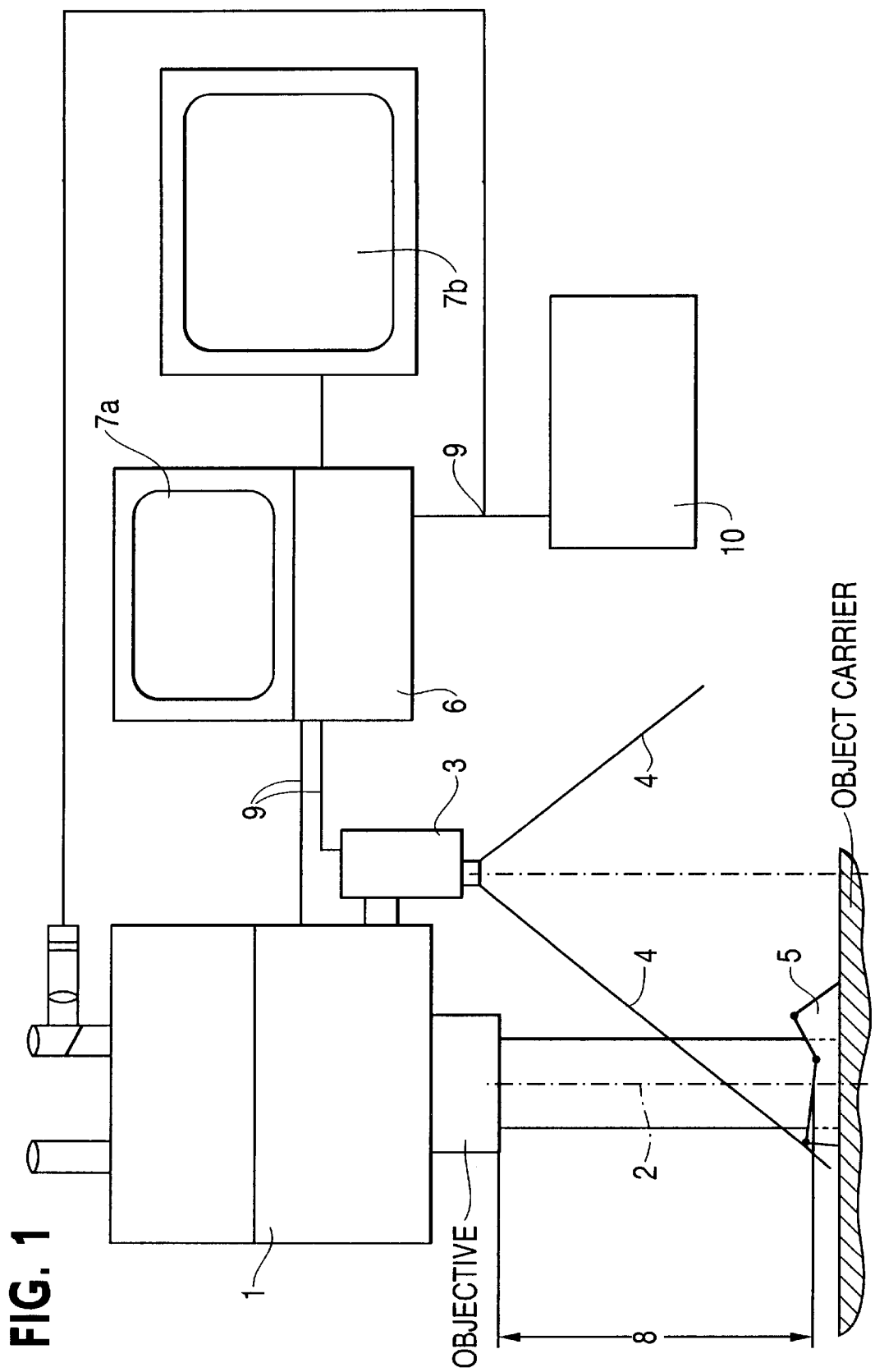

United States Patent [19]
Spink

[11] Patent Number: 6,081,370
[45] Date of Patent: Jun. 27, 2000

[54] DETERMINING THE POSITION OF A MOVING OBJECT

[75] Inventor: Roger Spink, Berneck, Switzerland

[73] Assignee: Leica Mikroskopie Systeme AG, Heerbrugg, Switzerland

[21] Appl. No.: 09/147,330

[22] PCT Filed: May 17, 1997

[86] PCT No.: PCT/EP97/02544

§ 371 Date: Dec. 3, 1998

§ 102(e) Date: Dec. 3, 1998

[87] PCT Pub. No.: WO97/46168

PCT Pub. Date: Dec. 11, 1997

[30] Foreign Application Priority Data

Jun. 3, 1996 [CH] Switzerland ............................ 1387/96

[51] Int. Cl.[7] .............................. G02B 21/36; G01B 9/08
[52] U.S. Cl. ......................... 359/369; 356/394; 382/151; 364/468.21
[58] Field of Search ..................................... 359/369, 372, 359/376; 356/392, 393, 394, 397; 382/151; 364/468.21

[56] References Cited

U.S. PATENT DOCUMENTS

| | | | |
|---|---|---|---|
| 4,989,082 | 1/1991 | Hopkins | 382/151 |
| 5,422,693 | 6/1995 | Vogeley et al. | 353/122 |
| 5,657,128 | 8/1997 | Muller et al. | 356/394 |
| 5,889,611 | 3/1999 | Zonneveld | 382/151 |

*Primary Examiner*—Jon Henry
*Attorney, Agent, or Firm*—Foley & Lardner

[57] ABSTRACT

A method for determining a position of a microscope (1) in space is disclosed. In image detecting unit (3) is fixed to the microscope. In an operating state, the image detecting unit detects a field of view of the microscope from an angle to an optical axis (2) and is connected to a computer which is equipped with an image recognition program and with comparison data for determination of the position of the microscope with respect to the field of view.

6 Claims, 1 Drawing Sheet

DETERMINING THE POSITION OF A MOVING OBJECT

The invention relates to a system with a microscope, and a method for the spatial determination of the position of a microscope. The object viewed through the microscope does not necessarily have to be a still object, but in the scope of this invention it can also be a moving object.

Especially in medicine, it is of great importance that, with simultaneous knowledge of the posit ion of the patient and the setting data of the microscope, it is possible to conclude the precise viewing location (operating field). This is becoming constantly more important in modern microsurgery. It is made possible for the surgeon to carry out an operation with great safety at the correct position. The importance of such knowledge is increasing with the advancing technology of making visible different image data, for example X-ray, CT, PE or MRI image data or the like in a microscope beam path, or superposing these on the image seen, so that the surgeon receives locally correctly presented comparison information concerning the operating field.

However, the invention can be beneficially used not only in medicine, but also in other areas where microscopic investigations are carried out.

The determination of the position of a microscope and thus of the operating field seen through the microscope, in accordance with the current state of the art, takes place for example by means of infrared positioning system. On the microscope there are disposed three infrared transmitters with encoded transmitted signals, the signals of which are detectedly infrared receivers disposed in space.

Somewhat older, but still used methods of determining position are: on the one hand the use of a microscope carrier frame, which at the joints has measuring elements (similar to a robot arm), which constantly follow the change in position of the microscope and determine the position by means of a microprocessor; on the other hand, the determination of the position by means of ultrasonic transmitters and sensors which are disposed on the microscope.

However, in the case of all previously known methods for determining position, problems arise in spite of fundamental functional competence. In the case of the older methods, it has to be borne in mind that the patient should not be influenced by the determination of position, and likewise any possible measurement results within the region viewed (e.g. site of operation) should not be influenced by the method of determining position. These two problems are solved with the use of the infrared positioning system. In this case, the problem does however arise that the infrared receivers are fitted at a spacing from the IR diodes or marking diodes of the microscope in space. A result of this is that an interfering influence may arise between transmitter and receiver. This can, for example, be caused by human who passes, or who brings an object, into the region of the signal exchange.

The last-mentioned problem has not been satisfactorily solved for quite a few applications. However, the location position of the patient relative to the microscope is an important item of information. Accordingly, the object of the invention is to provide a microscope with a system for determining position, which system permits no external interfering influences which may influence and falsify the determination of position. Accordingly, the intention is to know to where the microscope is precisely oriented, without in this case or for this purpose, as user, having to view through the microscope.

Furthermore, other image data (e.g. X-ray, CT or MRI image data) are to be capable of being superposed correctly in terms of position on the image viewed.

The object is achieved by the use, according to the invention, of at least one image recording unit on the microscope and at least one test body which serves for the calibration of the system and for measurement. In this case, the test body should be fixedly connectable to the object to be viewed, and specifically both in the course of microscopic examination and also previously in the course of other recording techniques such as, for example, MRI, X-ray, PE etc.

This additional problem is solved by the use according to the invention of at least one image detecting or recognition unit on the microscope and at least one comparison body or test body, which. is rigidly connected to the microscope or integrated into the latter. When This image recording unit views a known object, calibration can take place. If the microscope together with the image recording device then views an extraneous object which is however rigidly and visibly connected to the known object, the position or location of the extraneous object can be determined therefrom by means of image processing. If required, —possibly even just temporarily—the originally extraneous object can then be stored as a known—or calibration—object.

The image recording unit is fitted at a known angle, e.g. parallel to the beam path of the microscope. Both the sensor details in the case of specified settings of the microscope and also the image recording unit can be fed into a computer which computes from the delivered data the precise position of the operating field relative to the microscope. Other image data (e.g. MRI image data or the like) can be superposed correctly in terms of position, by means of displays and fade-in elements, on the image seen through the microscope. The field of view obtained in this way can be displayed on th computer screen or another connected monitor.

In a project, among others, at the Radiological Science Guys Hospital in London, "VISLAN Process and Project," it has been made known to identify by image processing, by means of camera, an object in space, which object was labeled by so-called FIDUCIALs but this technology alone does not permit the definition of on to which detailed region in the field of view or in the operating field a microscope is oriented, unless the microscope were also provided with comparable Fiducials and then a geometric computation were carried out, between the image information of one set of Fiducials and the image information in the case of the comparable Fiducials, as to where the microscope is viewing. Quite apart from this high degree of computing effort, in this case the mentioned problem of possible interference by persons or parts which pass between the Fiducials and the camera does again arise, so that a spatial location of the one or other set of Fiducials is made impossible.

With the invention, this disadvantage is eliminated; in this case, it is particularly favorable if the image recording unit has a field of view which is enlarged as compared with the microscope. Even if the image recording device is not connected to the microscope outside the latter, but is possibly integrate into the latter and possibly even views through the main objective itself, said device should have an enlarged field of view—e.g. by means of a different magnification—as compared with the microscope beam path, in order to guarantee a good circle of effectiveness of the determination of position.

In this case, the following detail s may be important: The direction of view of the microscope or of its main objective; the location of the main objective relative to the operating field, which location can be computed following knowledge of the direction e.g. via the Z spacing, which can be determined additionally by means of a separate measuring device or also from the image information through the test body or test bodies following knowledge of the setting data of the image recording device.

However, another matter of interest is where the viewing point lies in the horizontal viewing plane. In order to be able to deliver this information, the system is calibrated using a comparison body prior to each use. The comparison body includes points (e.g. corners, depressions) in respect of which all details are known, when it is situated in a positioned location. The system for determining position is set using these details, which are stored as comparison values in the computer.

In the course of calibration, the comparison body lies in prepositioned fashion under the microscope in the field of view of the image recording unit. The microscope is now positioned on to the known points. The comparison values, stored in the computer, of the points permit an arithmetic calibration balancing. From the details which the computer obtains through this procedure, any other viewed position can now be computed and its coordinates can be displayed e.g. on a screen.

Within the context of the invention, there is also a variant in which the image recording unit is directed not in the same direction as the microscope, but in another direction, e.g. to the ceiling of an operating theater, in order there, by reference to mat kings, to permit the determination of position.

An illustrative embodiment of the intention is shown in the drawing. The test body may have various contours. Any selectable systems, e.g. CCD cameras, may be selected as image recording units. How the microscope—computer and image recording unit—computer connections appear is dependent upon the systems used and the interface of the computer.

FIG. 1 shows a basic representation of the microscope according to the invention with the image recording unit, the connected computer and the comparison body.

FIG. 1 illustrates a principle of the invention. The representation shows a microscope 1 with its optical axis 2, in which the comparison body 5 lies. Parallel to the optical axis 2 there is fitted the image recording unit 3 in the field of view 4 of which the comparison body 5 likewise lies. The precise viewing position is computed using the object spacing 8 obtained via the microscope magnification and the data of the image recording unit 3, which are transferred via the connections 9 to the computer 6. Other image data 10 (e.g. X-ray, CT or MRI image data) can likewise be superposed thereon on the computer 6. The field of view obtained in this way can be displayed on the computer screen 7a and/or on an external monitor 7b.

Not shown, but conceivable, in addition to the image recording unit 3 according to the invention, are image sensors in the microscope beam path which make the seen images capable of being displayed on the monitor. It is likewise conceivable that the image information of the monitor 7 is reflected, by means of known measures, into the eyepiece beam path of the microscope 1. In this way, the microscope beam path together with the inserted other image data may be displayed on the computer screen (7a) and/or an external monitor (7b).

If the image recording device or the camera views through the main objective, the resultant advantage is that in the event of the use of a drape (sterile cladding of the microscope) there are no vision problems for the camera.

Within the context of the invention, there are also variants with more than one camera. In the event of the use of only one camera, a plurality of orientation points on a known object are of advantage, while in the event of the use of two or more cameras even a single marking point is sufficient.

In the case of cameras fitted in parallel, it is taken into consideration that the axis of the microscope should be parallel, in order to be able to carry out the image processing arithmetically without errors.

| LIST OF REFERENCE SYMBOLS | |
|---|---|
| 1 | microscope |
| 2 | optical axis |
| 3 | image recording unit |
| 4 | field of view of the image recording unit |
| 5 | comparison body |
| 6 | computer |
| 7a | computer screen |
| 7b | external monitor |
| 8 | object spacing |
| 9 | cable connections |
| 10 | source for other image data (e.g. X-ray, CT, PE or MRI image data or the like) |

What is claimed is:

1. A method for determining a position of a microscope in space, wherein an image detecting unit is fastened to the microscope in a fixed relative position, which in an operating state detects a field of view of the microscope from an angle to an optical axis of the microscope and is connected to a computer which is equipped with an image recognition program and with comparison data for determination of the position of the microscope with respect to the field of view.

2. A method according to claim 1, wherein a comparison body, which is adapted to be connected to a body to be viewed, lies within the field of view of the image detecting unit, said comparison body having spatial dimensions that are known and are stored in the computer and are acquired by the image detecting unit.

3. A method according to claim, 1 wherein a comparison body, contours of which are known and are stored in the computer, is presented to the microscope and the image detecting unit prior to use for calibration.

4. A method according to claim 2, wherein position data and magnification data of the microscope are obtained, modified by the computer, and presented superimposed in correct position with other image data on a display.

5. A method according to claim 4, wherein the other image data are reflected visibly for an observer, in an ocular ray path of the microscope.

6. A system with a microscope and an image detecting unit joined thereto in fixed relative position, both of which detect a field of view of the microscope in an operating state, wherein the image detecting unit detects at an angle to an optical axis of the microscope, and the image detecting unit is connected to a computer which comprises an image recognition program with comparison data for determining a position of the microscope with respect to a comparison body which is adapted to be connected to a body to be viewed and wherein geometrical dimensions of the comparison body are known and storable in the computer.

* * * * *